(12) United States Patent
Rielly et al.

(10) Patent No.: US 7,056,290 B2
(45) Date of Patent: Jun. 6, 2006

(54) CONTINUOUS DEPTH HARMONIC IMAGING USING TRANSMITTED AND NONLINEARLY GENERATED SECOND HARMONICS

(75) Inventors: Matthew Rielly, Seattle, WA (US); James Jago, Seattle, WA (US)

(73) Assignee: Koninklijke Philips Electronics, N.V., Eindhoven (NL)

(*) Notice: Subject to any disclaimer, the term of this patent is extended or adjusted under 35 U.S.C. 154(b) by 228 days.

(21) Appl. No.: 10/261,844

(22) Filed: Sep. 30, 2002

(65) Prior Publication Data

US 2004/0064043 A1 Apr. 1, 2004

(51) Int. Cl.
*A61B 8/00* (2006.01)
(52) U.S. Cl. .................................. 600/447
(58) Field of Classification Search ............. 600/437, 600/443, 447, 453–458; 128/916; 73/625–626; 310/334–336; 29/25, 35
See application file for complete search history.

(56) References Cited

U.S. PATENT DOCUMENTS

| | | | |
|---|---|---|---|
| 5,526,816 A | 6/1996 | Arditi | |
| 5,833,613 A | 11/1998 | Averkiou et al. | |
| 5,879,303 A | 3/1999 | Averkiou et al. | |
| 5,897,500 A * | 4/1999 | Zhao | 600/443 |
| 5,913,823 A * | 6/1999 | Hedberg et al. | 600/443 |
| 5,951,478 A | 9/1999 | Hwang et al. | |
| 6,027,448 A * | 2/2000 | Hossack et al. | 600/447 |
| 6,117,082 A | 9/2000 | Bradley et al. | |
| 6,120,448 A | 9/2000 | Bradley et al. | |
| 6,241,676 B1 * | 6/2001 | Savord | 600/447 |
| 6,283,919 B1 * | 9/2001 | Roundhill et al. | 600/447 |
| 6,309,356 B1 | 10/2001 | Ustuner et al. | |
| 6,312,379 B1 | 11/2001 | Bradley et al. | |
| 6,364,835 B1 | 4/2002 | Hossack et al. | |
| 6,440,075 B1 * | 8/2002 | Averkiou | 600/443 |
| 6,514,206 B1 * | 2/2003 | Maxwell et al. | 600/443 |
| 6,544,182 B1 * | 4/2003 | Averkiou | 600/455 |
| 6,605,043 B1 * | 8/2003 | Dreschel et al. | 600/459 |
| 6,656,123 B1 * | 12/2003 | Jensen et al. | 600/458 |
| 6,666,825 B1 * | 12/2003 | Smith et al. | 600/459 |
| 6,705,996 B1 * | 3/2004 | Kawagishi et al. | 600/458 |

\* cited by examiner

Primary Examiner—Francis J. Jaworski

(57) ABSTRACT

A system and method for ultrasonic harmonic imaging. The ultrasonic harmonic imaging system comprises a wideband phased-array transducer, a transmitter for transmitting waves into the tissue, a portion of which is at a fundamental frequency and a portion of which is at a harmonic of the fundamental frequency, a receiver for receiving ultrasonic responses from the tissue, a control system electrically coupled to the transmitter and the receiver for controlling operation of the transmitter and receiver, a video processor, and a monitor.

23 Claims, 3 Drawing Sheets

CONTINUOUS DEPTH HARMONIC IMAGING USING TRANSMITTED AND NONLINEARLY GENERATED SECOND HARMONICS

FIELD OF THE INVENTION

The present invention relates to tissue harmonic imaging (THI). More particularly, the invention relates to a system and method that utilizes a transmit beam comprising both the fundamental frequency and harmonics of the fundamental frequency to be respectively focused at different depths in order to realize return echoes comprising transmitted and non-linearly generated harmonics.

BACKGROUND OF THE INVENTION

Ultrasonic imaging has quickly replaced conventional X-rays in many clinical applications because of its image quality, safety, and low cost. The typical way of implementing ultrasonic imaging is to transmit a pulse at a given frequency and receive its echoes.

Ultrasonic images are typically formed through the use of phased or linear array transducer elements which are capable of transmitting and receiving pressure waves directed into a medium such as the human body. Such transducer elements normally comprise multielement piezoelectric materials, which materials vibrate in response to an applied voltage to produce the desired pressure waves. Regardless of the type of transducer element, these transducer elements may be further assembled into a housing, possibly containing control electronics, the combination of which forms an ultrasonic probe (or transducer).

Transducers (or ultrasonic probes) may then be used along with an ultrasonic transceiver to transmit and receive ultrasonic pressure waves through the various tissues of the body. The various ultrasonic responses may be further processed by an ultrasonic imaging system to display the various structures and tissues of the body.

Generally speaking, low frequency pressure waves provide deep penetration into the medium (e.g., the body), but produce poor resolution images due to the length of the transmitted wavelengths. On the other hand, high frequency pressure waves provide high resolution, but with poor penetration. Accordingly, the selection of a transmitting frequency has involved balancing resolution and penetration concerns.

In addition, THI provides for clutter suppression from reverberation reduction (e.g., from ribs) due to generation at a distance from the source, clutter suppression from side and grating-lobe reduction, contrast enhancement from the use of higher imaging frequencies (and the frequency dependence of backscatter) and a general IQ improvement from aberration (e.g., multi-path) reduction.

Recently, new methods have been studied in an effort to obtain both high resolution and deep penetration. One such method is known as harmonic imaging. Harmonic imaging is grounded on the phenomenon that objects, such as human tissues, develop and return their own non-fundamental frequencies, i.e., harmonics of the fundamental frequency. This phenomenon and increased image processing capabilities of digital technology make it is possible to excite an object to be imaged by transmitting at a low fundamental frequency ($f_o$) and receiving reflections at a higher frequency harmonic (e.g., $2f_o$) to form a high resolution image of an object. By way of example, a wave having a center frequency of 2 MHz can be transmitted into the human body and harmonic frequencies at integer multiples of the fundamental frequency, e.g., 4 MHz and 6 MHz, etc., can be received to form the image.

Transducers have been designed for transmit frequencies in the range of 2 MHz to 3 MHz for sufficient resolution of cardiac valves, endocardial borders and other cardiac structures. Lower transmit frequencies have been used for Doppler but not for B-mode imaging. Heretofore, transmit frequency selection has been determined based on the capabilities of fundamental response imaging which required relatively high fundamental frequencies in order to obtain adequate resolution for diagnostic purposes.

However, in order to achieve the benefits of transmitting at a lower frequency for tissue penetration and receiving a harmonic frequency for improved imaging resolution, broadband transducers are required which can transmit sufficient bandwidth about the fundamental frequency and receive sufficient bandwidth about the harmonic(s). The s4 transducer available with the SONOS™ 5500, an ultrasound imaging system manufactured by and commercially available from Agilent Technologies, U.S.A., has a suitable bandwidth to achieve harmonic imaging with a single transducer thus providing a significant clinical improvement. Furthermore, the combination of the s4 transducer and the SONOS™ 5500 provide multiple imaging parameter choices using a single transducer, thus providing a penetration choice as well as a resolution choice.

However, several problems exist with the current harmonic imaging technology due to the fact that current transducer designs have been based on fundamental imaging and not harmonic imaging. The goal with harmonic imaging is to generate harmonic signals in the body of high enough intensity to be above the noise floor of the system. A harmonic signal may be more than 20 dB down (the actual figure depends upon the path length and frequency, the maximum level of nonlinearly generated second harmonic in the tissue is −6 dB) from the fundamental backscatter and therefore wide dynamic range receivers are required. In the near-field, where little harmonic generation has occurred, and in the far-filed where attenuation has taken over, it is not uncommon for a harmonic response to be 30–40 dB down from the fundamental backscatter. It is critical that the magnitude of the harmonic signal generated in the body be over both the noise floor of the system. In order to improve harmonic imaging the problem of non-uniform harmonic generation needs to be addressed.

This is acutely so with respect to a lack of non-linear second harmonic signal response in the near field. A more continuous or substantial second harmonic return signal component in the near field is desirable.

Several patents have been granted focusing on overcoming the signal-to-noise problem with harmonic imaging. U.S. Pat. No. 5,740,128 to Hossack et al., teaches a transmit element that minimizes the energy transmitted into the body at the range of frequencies where a response generated harmonic is expected as the transmitted energy can not be distinguished from a generated harmonic signal. The techniques revealed by Hossack address the dynamic range between the transmitted or fundamental frequency and the harmonic signal response. Hossack's techniques do not address non-uniform harmonic signal responses in near-field and far-field imaging planes.

U.S. Pat. No. 5,410,516 to Uhlendorf et al., discloses contrast agent imaging along with single pulse excitation techniques such as harmonic imaging. Specifically, Uhlendorf teaches that by choosing a radio-frequency (RF) filter to selectively observe any integer harmonic (2nd, 3rd, etc.), subharmonic (e.g., 1/2 harmonic) or ultraharmonic (e.g., 3/2 harmonic) it is possible to improve the microbubble to tissue ratio. The second harmonic has proven most useful due to the large bubble response at this frequency as compared to higher order integer harmonics, subharmonics or ultraharmonics. The second harmonic also is most practical due to bandwidth limitations on the transducer (i.e., <70% bandwidth, where percent bandwidth is defined as the difference of the high corner frequency −6 dB point from the low corner frequency −6 dB point, divided by the center frequency). However, single pulse excitation techniques together with harmonic imaging suffer from poor microbubble-to-tissue ratio as large tissue integer-harmonic signals mask the signal generated by the contrast agent.

U.S. Pat. No. 5,558,092 to Unger et al., discloses methods and apparatus for performing diagnostic and therapeutic ultrasound simultaneously. Unger introduces a specialized transducer with "diagnostic" elements and "therapeutic" elements. The therapeutic elements are intended to rupture vesicles (microbubbles) containing drugs/genes or other therapeutic materials, while the diagnostic elements are available to monitor results of the rupture events. Unger teaches low frequency high power ultrasonic signals to enhance rupturing of the vesicles for therapeutic reasons. Unger's transducers are complicated, difficult to manufacture, and expensive. The transducers also suffer in performance from a typical phased-array transducer because the full aperture can not be used for imaging as a significant portion of the transducer is dedicated to therapeutic insonification.

U.S. Pat. No. 5,833,613 to Averkiou et at, teaches a multi-pulse transmission signal designed to minimize transmitted noise and to increase the harmonic signal. The technique transmits consecutive pulses with reversed polarities from one another into the body. Reflective addition of the pulses will subtract transmitted second harmonic reflections (undesired) and will cause the generated harmonic waveforms, which return to the transducer in phase, to add coherently thus increasing the signal-to-noise ratio. Like U.S. Pat. No. 5,740,128 to Hossack et al., Averkiou's multi-pulse technique does not address non-uniform harmonic signal responses. Averkiou's multi-pulse technique is susceptible to motion artifacts generated by each subsequent return of the multiple transmission pulses. In addition, Averkiou's multi-pulse technique increases signal-processing overhead, which leads to a decrease in the frame rate for real-time ultrasound diagnostic systems.

A second U.S. patent to Averkiou et al., U.S. Pat. No. 5,879,303, teaches a method for ultrasonic imaging using reflections from both the fundamental and one or more harmonic signals in the presence of depth dependent ultrasound signal attenuation. Averkiou et al. Determined that harmonics could be created as ultrasound waves passed through tissue and became distorted. The distortion was found to create harmonic signal components imaging with which is referred to in the art as tissue harmonic imaging (THI). Hence, the '303 patent teaches that images may be reconstructed to contain both fundamental, e.g., 3 MHz, and harmonic, 6 MHz, frequency components from a transmit signal which contains only the fundamental transmit frequency.

By transmitting energy only at the fundamental frequency, e.g., 3 MHz, and by removing reflections from the fundamental and using only generated harmonics to create the image, multi-path clutter from undesired structures in the near-field may be removed utilizing the inventive THI concepts set forth in the '303 patent. While the '303 patent discusses a need to reduce multi-path clutter in the near-field, the '303 patent fails to address the need to quickly generate harmonic signal responses in the near-field, where the generated harmonic signals are generally 30 dB down from the fundamental. The '303 patent also fails to address the need for deeper signal penetration in order to generate harmonic signal responses with a suitable energy level in the far-field where the energy is also more than 30 dB down.

U.S. Pat. No. 6,117,082 to Bradley et al., teaches medical diagnostic ultrasound imaging at a fractional harmonic such as $f_0/2$ or $3f_0/2$, where $f_0$ is the fundamental frequency of the transmit beam. To improve the fractional harmonic imaging, the '082 patent proposes adding a fractional harmonic seed component, for example, at $f_0/2$ or $3 f_0/2$. That is, the '082 patent teaches that adding a subharmonic seed signal with the fundamental frequency along with the fundamental transmit signal will cause the subharmonic of the fundamental transmit signal to develop more quickly. However, because of the time required to develop tissue harmonics, there is an inconsistency of energies of the different frequencies received back from the same tissue depths.

U.S. Pat. No. 6,283,919 B1, to Roundhill, et al., commonly owned and incorporated by reference herein in its entirety, teaches an ultrasonic diagnostic imaging system and method in the field of tissue harmonic imaging (THI) whereby both fundamental and harmonic components are returned in the echo signal and analyzed. The invention disclosed uses the harmonic echo signal components to reduce near-field or multi-path clutter in the ultrasonic image, such as that produced when imaging through narrow acoustic windows such as the ribs. The invention thereby allows imaging ay appreciable depths and substantially decreases the effects of depth-dependent attenuation.

U.S. Pat. No. 6,312,379 B1 to Bradley et al, discloses an ultrasound imaging method which includes transmitting a pre-distorted at least one of a plurality of waveforms as a function of non-linearity, e.g., a device non-linearity, a wavelength propagation non-linearity, etc. The transmitted waveform may comprise a fundamental spectral component and a harmonic spectral component from the transducer, where an attenuated normalized peak of the harmonic spectral component is reduced at a region spaced from the transducer as compared to the region adjacent the transducer. The transmitted waveform is preferably pre-distorted to include a harmonic spectral peak suppressed by about 4 dB or more at a region of interest spaced from the transducer relative a harmonic spectral peak at a region associated with transmission of a waveform comprising a fundamental spectral component adjacent the transducer.

Pending U.S. patent application Ser. No. 09/802,491, filed Mar. 9, 2001, commonly owned, and incorporated herein by reference in its entirety, discloses an ultrasonic imaging system and method wherein fundamental and harmonic components of the received signal are located in the transmit pass band. Pending U.S. patent application Ser. No. 10/026, 997, filed Dec. 19, 2001, commonly owned, and incorporated herein by reference in its entirety, discloses an ultrasonic imaging system and method which uses a small signal at a harmonic frequency for imaging blood vessels. That is, a low energy signal at the fundamental and a harmonic is focused on blood vessels until that time that the contrast agent appears, whereafter the composition of the transmitted signal is changed to insonify the CA.

A fundamental problem associated with the conventional THI is that it does not address focusing of the various frequency components at transmission to maximize return at various depths. That is, the prior art teaches that both the fundamental and harmonic frequencies are focused at the same depth. Because it takes some time for the tissue harmonic to develop, none or little harmonic signal energy is received from shallow depths. More particularly, while the conventional art may teach or suggest transmitting ultrasound energy with a beam including both fundamental and harmonic frequency components, the beam is always focused at the same depth. In such practice, however, the harmonic components, which take a finite time to develop, are found to be limited with respect to the near field. That is, the production of harmonics is a function of propagation path length so that in the near field, little harmonic signal is generated.

SUMMARY OF THE INVENTION

In response to these and other shortcomings of the prior art the present invention relates to an improved ultrasonic imaging system for harmonic imaging of an object in a medium using transmitted harmonic components, in addition to the fundamental, which harmonic components are directed or steered to, for example, the near field.

Briefly described, in architecture, the system can be implemented with a wideband transducer, e.g., a wideband phased-array transducer, a transmitter which generates electrical signals that may be converted by the transducer to fundamental and harmonic ultrasonic pressure waves for directed transmission into a medium, a receiver for receiving harmonic ultrasonic responses from at least one object in the medium, and a control system electrically coupled to the transmitter and the receiver for controlling operation of the transmitter and the receiver.

The present invention can also be viewed as providing a method for ultrasound imaging by which a signal is transmitted which includes both fundamental and harmonic frequency components. The harmonic components are focused or steered to at least one position in the field which is different than that position at which the fundamental is focused. For example, in one mode of operation, the fundamental is focused at a far field, and the harmonic, which is limited to one harmonic component, in particular, the second harmonic, is focused at the near field, or lower depths of penetration. The response or return echo signal comprises an increased amount of second harmonic energy from the shallow depth than would normally be received, and an amount non-linearly generated harmonic echoes from the deeper depths.

More particularly, a portion of the ultrasonic signal at the harmonic frequency is transmitted, simultaneously with a portion at the fundamental frequency, and focused at the shallow depth. The echoes at the harmonic frequency from this signal are used to image shallow depths. The fundamental may be focused at a greater depth, preferably at a depth greater than that normally directed to while performing conventional THI. Because the higher frequency transmitted second harmonic has a significantly lower depth penetration than the fundamental, most second harmonic received from the far field will be non-linearly generated whereas most second harmonic received from the near field will be transmitted second harmonic. The resultant image is a composite derived from harmonic energy returned from the near field, and harmonic energy returned from the far field, which has been generated through nonlinear propagation of the fundamental.

In another form, the present invention uses different temporal and spatial apodization functions for the fundamental and transmitted harmonic components.

In another form, this technique may be used in conjunction with pulse inversion techniques, where a pulse inversion scheme is activated as a function of receive focal depth. The near field transmitted harmonic image may them be combined with the nonlinear harmonic pulse inversion image.

Other systems, methods, features, and advantages of the present invention will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

Figure 1:
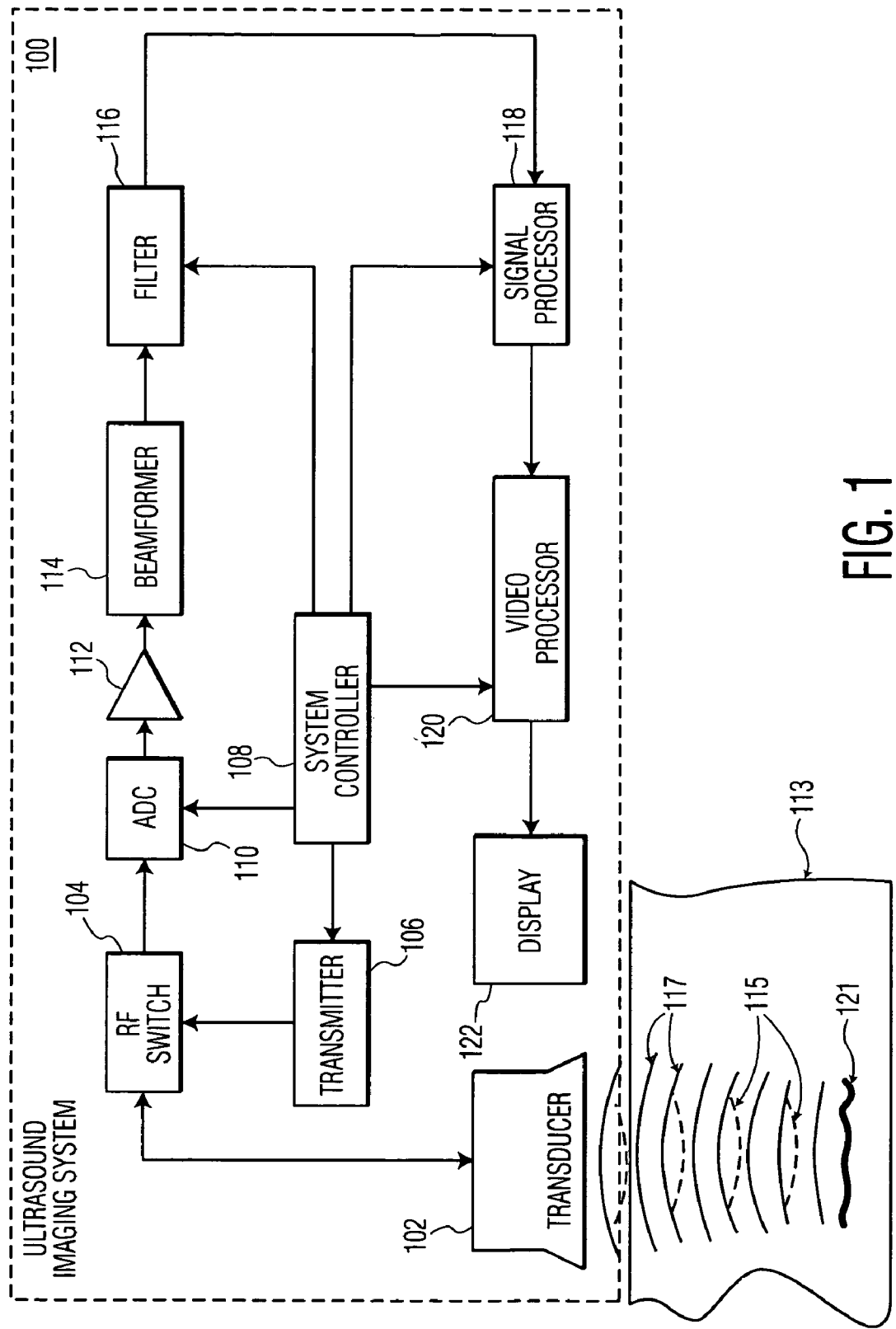
FIG. 1 is a block diagram of an ultrasonic imaging system consistent with the teachings of the present invention.

Having summarized various aspects of the present invention, reference will now be made in detail to the description of the invention as illustrated in the drawings. While the invention will be described in connection with these drawings, there is no intent to limit it to the embodiment or embodiments disclosed therein. On the contrary, the intent is to cover all alternatives, modifications and equivalents included within the spirit and scope of the invention as defined by the appended claims.

Turning now to the drawings, wherein like referenced numerals designate corresponding parts throughout the drawings, reference is made to FIG. 1, which illustrates a block diagram of an ultrasound imaging system capable of implementing the use of combined transmit pulses to introduce second harmonic energy into a patient along with a fundamental frequency transmit signal. That is, varying amounts of second harmonic may be added to the transmit beam on a per element basis, thus creating a transmit beam which is independent of the non-linearly generated second harmonic to create a more continuous transmit harmonic beam.

In this regard, an ultrasound imaging system 100 may comprise a transducer 102, a RF switch 104, a transmitter 106, a system controller 108, an analog to digital converter (ADC) 110, a time gain control amplifier 112, a beamformer 114, a filter 116, a signal processor 118, a video processor 120, and a display 122. The transducer 102 may be electrically coupled to RF switch 104. The RF switch 104 may be configured as shown with a transmit input coupled from the transmitter 106 and a transducer port electrically coupled to the transducer 102. The output of RF switch 104 may be electrically coupled to an ADC 110 before further processing by the time gain control amplifier 112. The time gain control amplifier 112 may be coupled to a beamformer 114. The beamformer 114 may be coupled to the filter 116. The filter 116 may be further coupled to a signal processor 118 before further processing in the video processor 120. The video processor 120 may then be configured to supply an input signal to a display 122. The system controller 108 may be coupled to the transmitter 106, the ADC 110, the filter 116, and both the signal processor 118 and the video processor 120 to provide necessary timing signals to each of the various devices.

As will be appreciated by persons having ordinary skill in the art, the system controller 108 can include one or more processors, computers, and other hardware and software components for coordinating the overall operation of the ultrasonic imaging system 100. In addition, it will be appreciated that the system controller 108 may include software which comprises an ordered listing of executable instructions for implementing logical functions, which can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. The computer readable medium can be, for instance, an electronic, magnetic, optical, electromagnetic, infrared, or semiconductor system, apparatus, device, or propagation medium.

The RF switch 104 isolates the transmitter 106 of the ultrasound imaging system 100 from the ultrasonic response receiving and processing sections comprising the remaining elements illustrated in FIG. 1. The system architecture illustrated in FIG. 1 provides an electronic transmit signal generated within the transmitter 106 that is converted to one or more ultrasonic pressure waves herein illustrated by ultrasound lines 115. When the ultrasound lines 115 encounter a tissue layer 113 that is receptive to ultrasound insonification the multiple transmit events or ultrasound lines 115 penetrate the tissue 113. As long as the magnitude of the multiple ultrasound lines 115 exceeds the attenuation affects of the tissue 113, the multiple ultrasound lines 115 will reach an internal target 121. Those skilled in the art will appreciate that tissue boundaries or intersections between tissues with different ultrasonic impedances will develop ultrasonic responses at harmonics of the fundamental frequency of the multiple ultrasound lines 115.

As further illustrated in FIG. 1, such harmonic responses may be depicted by ultrasonic reflections 117. It will be further appreciated that tissue insonified with ultrasonic waves develops harmonic responses because the compressional portion of the insonified waveforms travels faster than the rarefactional portions. The different rates of travel of the compressional and the rarefactional portions of the waveforms causes the wave to distort producing a harmonic signal which is reflected or scattered back through the various tissue boundaries. It is significant to note that while FIG. 1 illustrates only a second harmonic response to the incident multiple ultrasound lines 115 impinging the internal target 121 within the tissue layer 113, other harmonic responses may also observed. For example, nonlinear propagation of broadband signals may produce subharmonics in a sense. Nonlinear propagation is essentially the intermixing of all the frequency components present in the wave where the frequencies generated are the summation and difference frequencies of the components present in the broadband signal.

Those ultrasonic reflections 117 of a magnitude that exceeds the attenuation effects from traversing tissue layer 113 may be monitored and converted into an electrical signal by the combination of the RF switch 104 and transducer 102. The electrical representation of the ultrasonic reflections 117 may be received at the ADC 110 where they are converted into a digital signal. The time gain control amplifier 112 coupled to the output of the ADC 110 may be configured to adjust amplification in relation to the total time a particular ultrasound line 115 needed to traverse the tissue layer 113. In this way, response signals from one or more internal targets 121 will be gain corrected so that ultrasonic reflections 117 generated from relatively shallow objects do not overwhelm in magnitude ultrasonic reflections 117 generated from insonified objects further removed from the transducer 102.

The output of the time gain control amplifier 112 may be beamformed, filtered and demodulated via beamformer 114, filter 116, and signal processor 118. The processed response signal may then be forwarded to the video processor 120. The video version of the response signal may then be forwarded to display 122 where the response signal image may be viewed. It will be further appreciated by those of ordinary skill in the art that the ultrasonic imaging system 100 may be configured to produce one or more images and/or oscilloscopic traces along with other tabulated and or calculated information that would be useful to the operator.

Figure 2A:
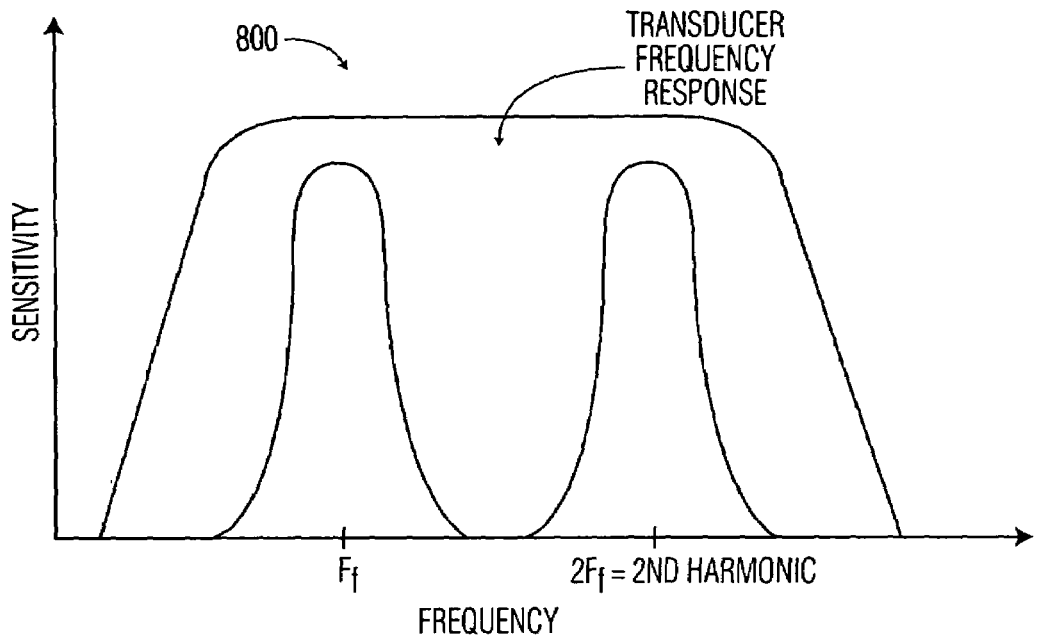
FIGS. 2A and 2B are schematic diagrams showing an ultrasound transducer which may be used with this invention.
Figure 2B:
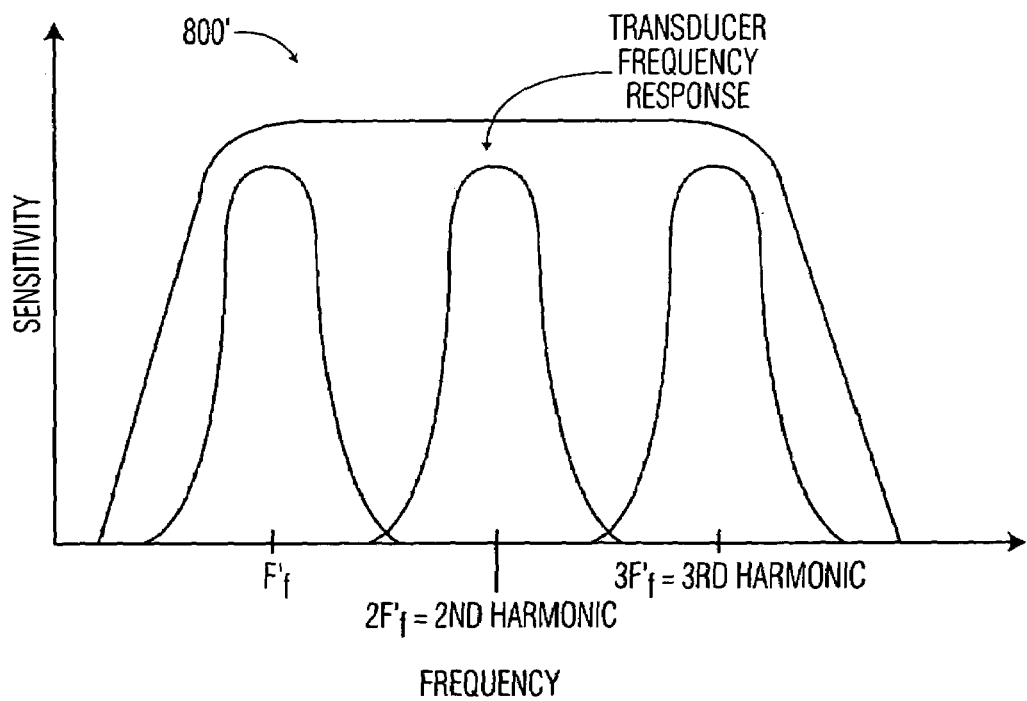

An ultrasonic imaging system 100 in accordance with the present invention can produce harmonic response signals in the far-field due to the nonlinear propagation of the lower transmit frequency. Transmitted harmonic signal may be used to generate harmonic signal in the near field, temporal or spatial apodization of the transmit signal as well as optimizing the spatial distribution of the harmonic in the near field. Transmit apodization may weight a subset of the transducer's 102 elements more than another subset of elements. The shifting of the fundamental frequency of a transducer 102 in accordance with the present invention to very low frequencies, such as those below 1.5 MHz, is illustrated in FIGS. 2A and 2B. The extra bandwidth of single crystal transducers and MUTs provides an additional degree of freedom for processing harmonic response signals over a wide frequency range.

Figure 3:
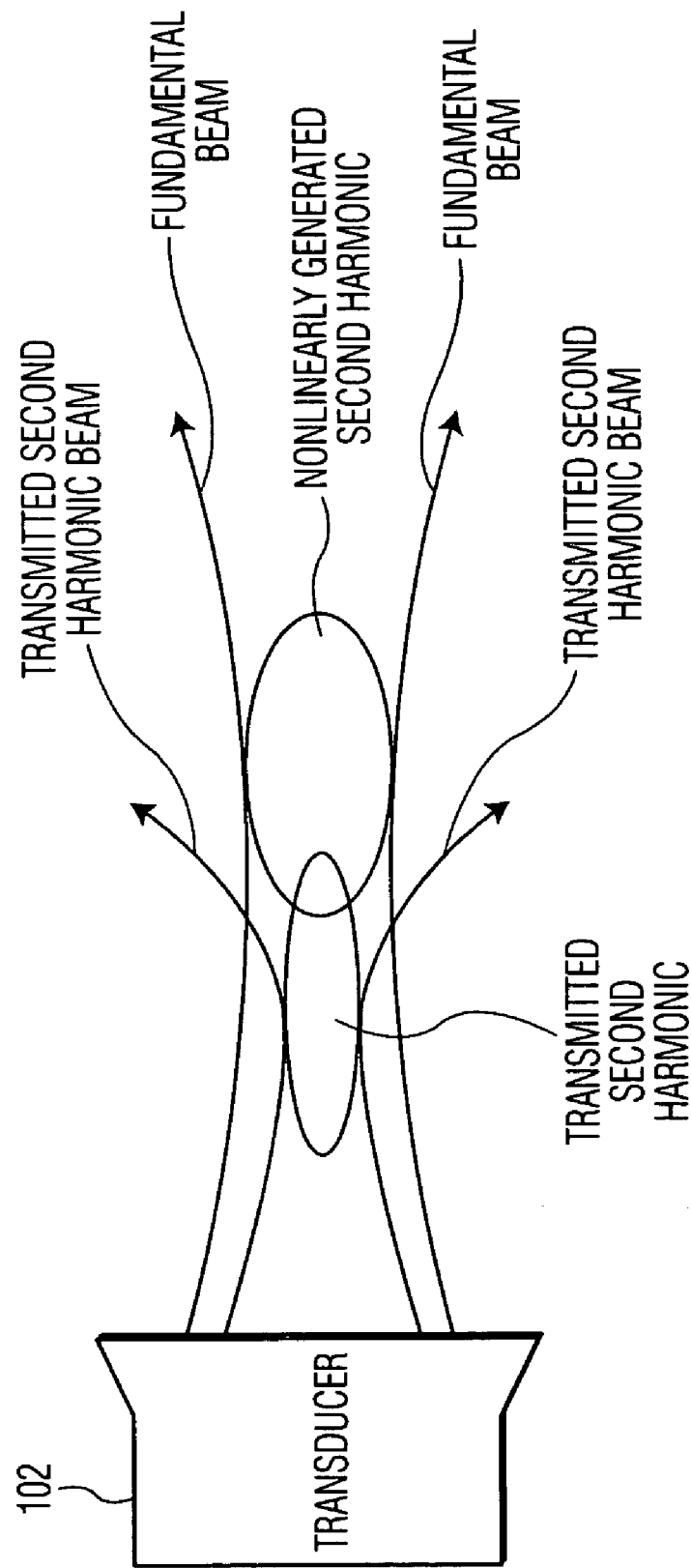
FIG. 3 is a schematic diagram showing an imaging field which is insonified in the near and far fields by focused or steered harmonic energy, and fundamental energy, respectively.

FIG. 3 is a schematic diagram, which shows the effective penetration of the combined frequency signal proposed hereby. That is, varying amounts of at least one harmonic of the fundamental frequency is added to the transmit beam on a per element basis, resulting in a transmit beam which is independent of non-linearly generated equivalent harmonics, e.g., the second harmonic received in the return echo. The harmonic portion of the transmit beam may be focused at a depth which is different than the depth at which the fundamental components are directed. Indeed, the focal gain of the transmitted harmonic beam may be optimized such that the degree of field divergence beyond the focal plane ensures that there will be minimal transmitted second harmonic in the focal plane of the fundamental. The result is a more continuous transmit harmonic beam, and a better composite image than can be realized with conventional THI imaging techniques and apparatus.

As mentioned above, little harmonic generation takes place in the shallow depths. More particularly, most second harmonic generation takes place at the final axial maximum of the fundamental field. As a result, a THI image may give an impression of a split in image quality between the fundamental axial position where non-linear based second harmonic generation largely takes place, and the near field where nonlinear second (and higher) harmonic generation is limited.

In principle, any method of this invention, and any system, which implements same, increases the depth of the field of the harmonics, particularly, the second harmonic, by introducing a second, very shallow, strongly "focused" harmonic beam. This second focal zone is used for a very short range (and therefore, time). The first focal zone is used beyond the shallow depth, and comprises (but not in all cases is limited to) the fundamental frequency. Because of the strong focus and short range of the first focal zone, the line period may be short with little effect on the final frame rate. In this method, both images are formed from non-linearly generated harmonic, and thus both images benefit from the image enhancements associated with the properties of non-linear generation.

While particular embodiments of the invention have been disclosed in detail in the foregoing description and drawings for purposes of example, it will be understood by those skilled in the art that variations and modifications thereof can be made without departing from the spirit and scope of the invention as set forth in the following claims.

What is claimed is:

1. An ultrasonic imaging system for focused harmonic imaging, comprising:
    a transmitter configured for generating ultrasound which includes a signal component at a fundamental frequency and at least one signal component at at least one harmonic of the fundamental frequency;
    a wideband transducer configured for converting the ultrasound signal from the transmitter having the included signal components into transmitted acoustic pressure waves including a first portion corresponding to the fundamental frequency and a second portion corresponding to the at least one harmonic frequency of the fundamental frequency, and for directing the first portion and second portion, respectively, to a, first focal zone, and a second focal zone, said transducer further configured for receiving and converting a fundamental frequency response and at least one harmonic acoustic response from the transmitted acoustic pressure waves into at least one response signal;
    a receiver for receiving at least one response signal;
    a control system electrically coupled to said transmitter and said receiver, said control system used to control the operation of said transmitter and said receiver;
    a video processor for converting the at least one response signal to a display signal; and
    a monitor for converting the display signal into an image.

2. The system of claim 1, wherein the transducer has a bandwidth of greater than approximately 70 percent, where percent bandwidth comprises the difference between a high corner −6 dB frequency and a low corner −6 dB frequency, the difference divided by a center frequency of the transducer bandwidth.

3. The system of claim 2, wherein the at least one signal component is the second harmonic.

4. The system of claim 1, wherein the transducer has a transmit bandwidth of greater than approximately 25 percent, where percent transmit bandwidth comprises the difference between a high corner transmit −6 dB frequency and a low corner transmit −6 dB frequency, the difference divided by the transmit frequency.

5. The system of claim 1, wherein the second portion of the acoustic pressure wave is directed to the near field and the first portion of the acoustic pressure waves is directed to the far field.

6. An ultrasonic imaging system for focused harmonic imaging, comprising:
    A transmitter for generating ultrasound which includes a signal component at a fundamental frequency and at least one signal component at at least one harmonic frequency of the fundamental frequency;
    a wideband transducer capable of converting the ultrasound signal from the transmitter into transmitted acoustic pressure waves including a first portion corresponding to the fundamental frequency and directing the first portion to a first focal zone, and including a second portion corresponding to the at least one harmonic frequency of the fundamental frequency and directing the second portion to a second focal zone, said transducer further capable of receiving and converting a fundamental frequency response and at least one harmonic acoustic response from the transmitted acoustic pressure waves into at least one response signal;
    a receiver for receiving at least one response signal;
    a control system electrically coupled to said transmitter and said receiver, said control system used to control the operation of said transmitter and said receiver;
    a video processor for converting the at least one response signal to a display signal; and
    a monitor for converting the display signal into an image, wherein the control system implements a pulse inversion scheme activated as a function of a focal depth of the second focal zone such that the second focal zone transmitted harmonic image may be combined with the nonlinear harmonic pulse inversion image.

7. A wideband phased-array transducer configured to convert an input ultrasound signal comprising a transmitted harmonic and fundamental frequency component into acoustic pressure waves including first and second wave portions to be focused at first and second focal zones, respectively, said transducer configured to receive and convert a transmitted harmonic and at least one non-linearly generated harmonic acoustic response from the transmitted acoustic pressure waves into at least one response signal.

8. The transducer of claim 7, wherein the harmonic is the harmonic frequency component is a second harmonic of the fundamental frequency.

9. The transducer of claim 7, wherein the first wave portion of the acoustic pressure wave is directed to the near field and the second wave portion is directed to the far field.

10. The transducer of claim 7, having a bandwidth comprising a transmit and a receive bandwidth and a center frequency, the bandwidth being greater than approximately 70 percent, where percent bandwidth comprises the difference between a high corner −6 dB frequency and a low corner −6 dB frequency, the difference divided by the center frequency.

11. The transducer of claim 10, wherein the transmit bandwidth is greater than 25 percent, where percent transmit bandwidth comprises the difference between a high corner transmit −6 dB frequency and a low corner transmit −6 dB frequency, the difference divided by the transmit frequency.

12. The transducer of claim 10, wherein the receive bandwidth is greater than 25 percent, where percent receive bandwidth comprises the difference between a high corner receive −6 dB frequency and a low corner receive −6 dB frequency, the difference divided by the receive frequency.

13. The transducer of claim 10, wherein the element array comprises at least two matching layers.

14. The transducer of claim 10, wherein the element array comprises at least three matching layers.

15. The transducer of claim 10, wherein the element array is constructed of materials comprising a single crystal.

16. The transducer of claim 10, wherein the transducer is a micro-machined ultrasonic transducer (MUT).

17. A method for detecting an ultrasonic harmonic response comprising:
   insonifying a tissue of interest with a pressure wave that emanates, from a wideband phased-array transducer, comprising a first portion with a fundamental frequency focused to a first focal zone and a second portion with a harmonic of the fundamental frequency focused to a second focal zone; and
   measuring a response to the transmitted second portion of the pressure wave returned from the second focal zone, and a harmonic response to the first portion of the pressure wave, only at substantially the harmonic frequency.

18. The method of claim 17, wherein the harmonic is the second harmonic of the fundamental frequency.

19. The method of claim 17, wherein the second portion of the acoustic pressure wave is directed to the near field and the first portion is directed to the far field.

20. The method of claim 17, wherein the step of measuring requires that the wideband, phased-array transducer have a bandwidth comprising a transmit and a receive bandwidth and a center frequency, the bandwidth greater than 70 percent, where percent bandwidth comprises the difference between a high corner −6 dB frequency and a low corner −6 dB frequency, the difference divided by a center frequency of the transducer bandwidth.

21. The method of claim 17, wherein the step of insonifying includes implementing a pulse inversion scheme activated as a function of receive focal depth such that any signal energy received from the near field is combined with any signal energy detected at harmonic frequencies of the fundamental frequency.

22. An ultrasonic imaging system for focused harmonic imaging, comprising:
   a transmitter configured for generating, for conversion by a wideband transducer, ultrasound which includes a first signal at a fundamental frequency and at least a second signal at at least one harmonic of the fundamental frequency;
   said wideband transducer configured for converting the ultrasound signals from the transmitter into acoustic pressure waves including a first portion corresponding to the first signal and a second portion corresponding to the second signal, which first and second portions are transmitted sequentially in time and directed respectively to a first and second focal zone, said transducer further capable of receiving and converting a transmitted harmonic response and at least one harmonic acoustic response from the transmitted acoustic pressure waves into at least one response signal;
   a receiver for receiving at least one response signal;
   a control system electrically coupled to said transmitter, said receiver, and said receiver, and said wideband transducer, said control system used to control the operation of said transmitter and said receiver and said wideband transducer;
   a video processor for converting the at least one response signal to a display signal; and
   a monitor for converting the display signal into an image.

23. The method of claim 17, said measuring being accomplished with a wideband phased-array transducer.

* * * * *